United States Patent
Khatib

(10) Patent No.: US 9,856,531 B2
(45) Date of Patent: *Jan. 2, 2018

(54) METHODS AND COMPOSITIONS FOR GENETICALLY DETECTING IMPROVED MILK PRODUCTION TRAITS IN CATTLE

(71) Applicant: WISCONSIN ALUMNI RESEARCH FOUNDATION, Madison, WI (US)

(72) Inventor: Hasan Khatib, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,810

(22) Filed: Jan. 8, 2016

(65) Prior Publication Data

US 2016/0115557 A1    Apr. 28, 2016

Related U.S. Application Data

(60) Division of application No. 12/981,529, filed on Dec. 30, 2010, now Pat. No. 9,371,562, and a division of application No. 11/869,464, filed on Oct. 9, 2007, now Pat. No. 7,888,021, and a continuation of application No. 10/726,571, filed on Dec. 4, 2003, now abandoned.

(51) Int. Cl.
| | |
|---|---|
| *A61D 19/02* | (2006.01) |
| *A61D 19/04* | (2006.01) |
| *C12Q 1/68* | (2006.01) |
| *C12P 19/34* | (2006.01) |
| *C07H 21/04* | (2006.01) |

(52) U.S. Cl.
CPC ............ *C12Q 1/6876* (2013.01); *A61D 19/02* (2013.01); *A61D 19/04* (2013.01); *C07H 21/04* (2013.01); *C12Q 1/6888* (2013.01); *C12Q 2600/124* (2013.01); *C12Q 2600/156* (2013.01); *C12Q 2600/172* (2013.01)

(58) Field of Classification Search
CPC ........ A61D 19/02; A61D 19/04; C07H 21/04; C12Q 2600/124; C12Q 2600/156; C12Q 2600/172
See application file for complete search history.

(56) References Cited

PUBLICATIONS

Lohuis M.M. Theriogeneology, 43:51-60 (1995).*

* cited by examiner

*Primary Examiner* — Stephen Kapushoc
(74) *Attorney, Agent, or Firm* — Kening Li; Miller Canfield

(57) ABSTRACT

An isolated nucleic acid molecule comprising a polymorphic site selected from the group consisting of positions 164, 269, 284, 407 and 989 of SEQ ID NO: 1, an array or a kit comprising the same. Also provided are a method for detecting single nucleotide polymorphism (SNP) in bovine proteinase inhibitor (PI) gene, a method for haplotyping a bovine cell, a method for progeny testing of cattle based on said haplotyping, a method for selectively breeding of cattle based on haplotyping a parent animal. The present invention further provides a method for testing a dairy cattle for its milk production trait, comprising haplotyping its cells, wherein a cattle having haplotypes 1, 3, 4 or 5 indicates that the cattle has desirable milk production trait. Haplotype 1 indicates that the cattle has the most desirable milk production trait.

6 Claims, 2 Drawing Sheets

```
                                          Start, 33
  1 gaccagccct gacctaggac agtgaatcga taatggcact ctccatcacg cggggccttc
 61 tgctgctggc agccctgtgc tgcctggccc ccatctccct ggctggagtt ctccaaggac 164
121 acgctgtcca agagacagat gatacatccc accaggaagc agcgtgccac aagattgccc
181 ccaacctggc caactttgcc ttcagcatat accaccattt ggctcatcag tccaacacca 269                  284
241 gcaacatctt cttctccccc gtgagcatgg cttcagcctt tgcgatgctc tccctgggag
301 ccaagggcaa cactcacact gagatcctga agggctggg  tttcaacctc actgagctcg 407
361 cagaggctga gatccacaaa ggctttcagc atcttctcca caccctgaac cagccaaacc
421 accagctgca actgaccact ggcaatggtc tgttcatcaa tgagagtgca aagctagtgg
481 atacgttttt ggaggatgtc aagaacctgt atcactccga agccttctcc atcaacttca
541 gggatgctga ggaggccaag aagaagatca acgattatgt agagaaggga agccatggaa
601 aaattgtgga gttggtaaag gttcttgacc caaacacagt ttttgctctg gtgaattaca
661 tttccttta aggaaaatgg gagaagccct tcgagatgaa gcacaccaca gagagggact
721 tccatgtgga cgagcaaacc actgtgaagg tgccatgat gaaccgcctg ggcatgtttg
781 acctccacta ctgcgacaag ctcgccagct gggtgctgct gttggactac gtgggcaacg
841 tcaccgcctg cttcatcctg cccgacctgg ggaaactgca gcagctggag gacaagctca
901 acaacgaact cctcgccaag ttcctggaaa agaaatatgc aagttctgcc aatttacatt 989
961 tgcccaaact gtccatttct gaaacgtagg atctaaaaag tgtcctgggc gatgtgggca
1021 tcaccgaggt cttcagcgat agggctgacc tctcagggat caccaaggaa cagcctctga
1081 aggtgtccaa ggctctccac aaggctgcac tgaccatcga tgagaaaggg acagaagctg
1141 tcgggtccac gtttctggaa gccatcccca tgtcccttcc cccagacgtc gagttcaaca
1201 gaccctcct ctgcatcctc tacgacagaa acaccaaatc tccctcttc gtgggaaagg stop, 1283
1261 tggtgaatcc cacccaagcc taactgcctc tcggagttca gccttcccct cccaggccag poly A signal
1321 gtcccccac tccctccatg gcattaaagg atgactgacc tagccccgaa aaaaaaaaaa
```

Figure 1

```
  1 cagaccgacc cgggagctgc cacatctggt tcagtcagag ggtgggggga tagacccacc
 61 gaccacggcc atgaccgctg tgtgtctgct tccaacagag gccagaatgc atgcacgtgg
121 taccaggcag actccatggg agggctggtg cccaggggtr aggagtgaaa gtcctgtcct
181 tgaggacgtc ctccccagcc tggaaactgc ccgttcctgg tgcacaggga aagcaatgtc
241 aaattcatgt tgttggcaaa cccagaaaga agaggatgga cttttggca aaggtggcag
301 ttgaatgtag attacaggat agagtgtgga ttacaggcta aaaagtccac ggcaggatgg
361 gggcggggga ggggaggata atgcttggag cattatccaa gataatgctg aaaaagccaa
421 cgcccagagc aggaaactcc agcacctgtt tgaggctggt tctgattcct ctgtcattag
481 atgagtgtgg ttcgaccagg tccccatcat gcactccata tcagtacctg tctctgtgtt
541 tgtagatatg cccaggcccg gatgagcaat tttatcatgt ataacataaa acaaagatga
601 aaatacagaa aagtactcct cacgccctct acagacgtca ctcaggacct accaccacac
661 cccacagtcc cctgggatcc tggccctggg ggagtcccag tctagcgggt gtgatgaaac
721 cctacaggga agtagtgagt acagtccttc cagaagacac cccagatctc caggaggcct
781 tctcagagga ggtggccctt gagaggctct gcaggacaag aggatggccc tgattctaat
841 atcctctgac cctgggcata gaggaactaa aagtggaata aaccaaagtg tgagagcacg
901 gggagagggc accaactgga aagaacaacc ggaaaaggaa gctctttcac tctgtgactt
961 ttttttttcc actacag
```

Figure 2

METHODS AND COMPOSITIONS FOR GENETICALLY DETECTING IMPROVED MILK PRODUCTION TRAITS IN CATTLE

This invention was made with United States government support awarded by USDA/CSREES, under the grant number 05-CRHF-0-6055. The United States may have certain rights in this application.

FIELD OF THE INVENTION

The present invention relates to a method of cattle progeny testing using molecular genetic methods by assaying for the presence of at least one genetic marker which is indicative of improved milk production and reproduction traits, including milk yield and milk composition, somatic cell score, productive life, and daughter pregnancy rate.

BACKGROUND OF THE INVENTION

Dairy cows are significant investments for dairy farmers, and enormous efforts, such as animal breeding and artificial insemination, have been and continue to be invested in ensuring that the animals have high and sustained productivity, and that the milk produced are of high quality. A successful breeding family is the Holstein line derived from Carlin-M Ivenhoe Bell. More than 25% of the highest total performance index Holstein bulls in the United States are progenies of this individual.

Traditional breeding techniques involve the studying of sire progenies, and evaluating their milk production ratings (transmitting abilities) to guide further breeding. This standard technique requires years to evaluate the true genetic value by progeny testing each bull. Many cows must be bred and give birth to offspring. The females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of the environmental and developmental variants. There is thus a need for a method of genetically evaluating cattle to enable breeders to more accurately select animals at both the phenotypic and the genetic level.

Marker-assisted selection can lower the high cost of progeny testing currently used to improve sires, since young bull progeny could be evaluated immediately after birth, and young bulls that are determined by genetic testing to have undesirable markers would never be progeny tested or even prior to birth, for the presence/absence of the marker. Therefore, there is also a need for genetic markers for improved milk production traits.

SUMMARY OF THE INVENTION

The present invention provides for an isolated nucleic acid molecule comprising a polymorphic site selected from the group consisting of positions 164, 269, 284, 407 and 989 of SEQ ID NO: 1 and at least 17 contiguous bases of SEQ ID NO: 1 adjacent to the polymorphic site, wherein the nucleic acid molecule comprises i) an adenine base at position 164 of SEQ ID NO: 1; ii) a guanine base at position 164 of SEQ ID NO: 1; iii) a cytosine base at position 269 of SEQ ID NO: 1; iv) a thymine base at position 269 of SEQ ID NO: 1; v) a guanine base at position 284 of SEQ ID NO: 1; vi) a thymine base at position 284 of SEQ ID NO: 1; vii) a guanine base at position 407 of SEQ ID NO: 1; viii) a cytosine base at position 407 of SEQ ID NO: 1; ix) a cytosine base at position 989 of SEQ ID NO: 1; or x) a thymine base at position 989 of SEQ ID NO: 1. It is recognized that SEQ ID NO: 1 is already known, and the nucleic acid molecule therefore does not encompass one that consists of SEQ ID NO: 1.

Preferably, the nucleic acid molecule which comprises at least 15, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

The present invention also provides an array of nucleic acid molecules comprising at least two nucleic acid molecules described above.

The present invention further provides a kit comprising a nucleic acid molecule of claim 1, and a suitable container.

Also provided is a method for detecting single nucleotide polymorphism (SNP) in bovine proteinase inhibitor (PI) gene, wherein the PI gene have a nucleic acid sequence of SEQ ID NO: 1, the method comprising determining the identity of a nucleotide at position 164, 269, 284, 407 or 989, and comparing the identity to the nucleotide identity at a corresponding position of SEQ ID NO: 1. Preferably, the identity of at least two positions of positions 164, 269, 284, 407 and 989 are determined. More preferably, the identity of all of positions 164, 269, 284, 407 and 989 are determined.

In another embodiment, the present invention provides a method for haplotyping a bovine cell, comprising determining the identity of the nucleotides of at least two positions of 164, 269, 284, 407 and 989 of bovine PI gene having a sequence of SEQ ID NO: 1, and comparing the identities at the respective positions to that shown in Table 1 below. Suitable bovine cell may be an adult cell, an embryo cell, a sperm, an egg, a fertilized egg, or a zygote. The identity of the nucleotide may be determined by sequencing the PI gene, or a relevant fragment thereof, isolated from the cell. The PI gene or a relevant fragment thereof is isolated from the cell via amplification by the polymerase chain reaction (PCR) of genomic DNA of the cell, or by RT-PCR of the mRNA of the cell. Preferably, the PCR or RT-PCR is conducted with a pair of primers selected from the group consisting of (1) SEQ ID NO: 2 and SEQ ID NO: 3; and (2) SEQ ID NO: 4 and SEQ ID NO: 5. In a preferred embodiment, both copies of the PI gene in the cell are haplotyped.

In a further embodiment, the present invention provides a method for progeny testing of cattle, the method comprising collecting a nucleic acid sample from said progeny, and haplotyping said nucleic sample as described above.

Further provided is a method for selectively breeding of cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and haplotyping said developing embryo, and terminating pregnancy if said developing embryo is not haplotype 1, 3, 4 or 5. Preferably, pregnancy is terminated if the embryo is not haplotype 1.

In a preferred embodiment, the method is used for selectively breeding dairy cattles, comprising selecting a bull that is homozygously haplotype 1 and using its semen for fertilizing a female animal. More preferably, the female animal which is also homozygously haplotype 1. MOET procedure may be preferably used for the selective breeding.

The present invention also provides a method for testing a dairy cattle for its milk production trait, comprising haplotyping its cells, wherein a cattle having haplotype 1, 3, 4 or 5 indicates that the cattle has desirable milk production trait. Preferably, the test is for a cattle having haplotype 1 which indicates that the cattle has desirable milk production trait, health and reproduction traits. Haplotype 1 is associated with high milk protein percentage, high productive life, low somatic cell score, and high daughter pregnancy rate. Haplotype 3 is associated with milk fat. Haplotype 4 is associated with high milk yield, high somatic cell score and low daughter pregnancy rate. Haplotype 5 is associated with high milk yield, low fat percentage, low protein percentage, high somatic cell score and low daughter pregnancy rate. Thus it would be desirable to make selection decisions on haplotype 1 that does not show any negative effects.

DESCRIPTION OF THE DRAWINGS

FIG. 1 shows the PI gene sequence (SEQ ID NO: 1) where the relevant polymorphic sites are shown.

FIG. 2 shows the novel sequence of an intron of bovine PI gene (SEQ ID NO: 6).

DETAILED DESCRIPTION OF THE INVENTION

The present inventor used the positional candidate gene approach and the positional comparative candidate gene analysis to study the association of the proteinase inhibitor (PI) gene with milk production and reproduction traits in Holstein dairy cattle. In principle, once quantitative trait loci (QTL) are mapped to a chromosomal region, possible candidate genes affecting the trait of interest can be identified. Using this approach, six haplotypes were identified (Table 1), and statistically significant correlations were found to exist between several milk production traits and the haplotypes, especially haplotypes 1, 3, 4 and 5 (See Tables 4, 5 in the Examples below). Particularly, haplotype 1 has been shown to have significant correlation with all of the following traits: milk protein percentage, productive life of the animal, milk somatic cell score (SCS), and daughter pregnancy rate (DPR) (See Table 3 in the Examples below for details).

The present invention discloses that haplotype 1 does not show any negative effects. Therefore it is particularly preferred to select for individuals homozygous for haplotype 1, which would increase the effect of the haplotype. Because haplotype 1 is associated with more than one trait at the same time, selection for haplotype 1 is equal to selection for multiple genetic markers. This is the first time that such a gene or genetic marker having multiple effects is found in cattle or any other livestock species.

TABLE 1

Haplotypes of Bovine PI Gene

| POSITION | 164 | 269 | 284 | 407 | 989 |
|---|---|---|---|---|---|
| "Wild type" | G | C | G | G | C |
| Haplotype 1 (ACGCT) | A | C | G | C | T |
| Haplotype 2 (GTTGT) | G | T | T | G | T |
| Haplotype 3 (GCGGT) | G | C | G | G | T |
| Haplotype 4 (GTTGC) | G | T | T | G | C |
| Haplotype 5 (GCGGC) | G | C | G | G | C |
| Haplotype 6 (ACGCC) | A | C | G | C | C |

The term "wild-type" is used to refer to the reference coding sequences of the PI gene as shown in FIG. 1. It has been found that specific sites in the PI gene sequence are polymorphic. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the haplotypes of the PI gene, which are found to have strong correlation to milk production traits.

Table 1 provides the various polymorphic sequences of the bovine PI gene. The provided sequences also encompass the complementary sequence corresponding to any of the provided polymorphisms. In order to provide an unambiguous identification of the specific site of a polymorphism, the numbering of the original PI sequence in the GenBank is shown in FIG. 1 and is used. The PI exon sequences have been published.

The present inventor sequenced an intron of the PI gene. The sequence of the intron is provided in FIG. 2 (SEQ ID NO: 6). This intron sequence is used to design primers PI10 which allows genomic amplification of the fragment containing the SNP at position 989.

The present invention provides nucleic acid based genetic markers for identifying bovine animals with superior reproduction and milk production traits. In general, for use as markers, nucleic acid fragments, preferably DNA fragments, will be of at least 12 nucleotides (nt), preferably at least 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at position 164 is G or A. An oligonucleotide probe can be used for such purpose. Preferably, the oligonucleotide probe will have a detectable label, and contains an A at the corresponding position. Experimental conditions can be chosen such that if the sample DNA contains an A, then hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the PI gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms, and may include all or a subset of the polymorphisms listed in Table 1.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 164 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the PI gene of the sample of interest may be amplified via PCR and directly sequenced, and the sequence be compared to the haplotype information of Table 1. In this case, two sets of PCR primers are preferably used for optimal amplification and to avoid the need to sequence an unnecessarily long fragment. The region that contains positions 164-407 can be amplified with a first set of primers (e.g. SEQ ID NO: 2 and 3), and the region containing position 989 can be amplified separately with a second set of primers (e.g. SEQ ID NO: 4 and 5). It is readily recognized that numerous other primers can be devised to achieve the same objectives. The sequence information will allow the determination of all six polymorphic site shown in Table 1. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype and/or haplotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The term "haplotype" refers to the actual combination of alleles on one chromosome. At the DNA level, it refers to a sequence of nucleotides found at two or more polymorphic sites in a locus on a single chromosome. As used herein, haplotype includes a full-haplotype and/or a sub-haplotype. Full-haplotype is the 5' to 3' sequence of nucleotides found at all polymorphic sites examined in a locus on a single chromosome from a single individual, while sub-haplotype refers to the 5' to 3' sequence of nucleotides seen at a subset of the polymorphic sites examined in a locus on a single chromosome from a single individual. Relatedly, the term "haplotype pair" refers to the two haplotypes found for a locus in a single individual. "Haplotyping" is a term for a process for determining one or more haplotypes in an individual and includes use of family pedigrees, molecular techniques and/or statistical inference.

The present invention is suitable for identifying a bovine, including a young or adult bovine animal, an embryo, a semen sample, an egg, a fertilized egg, or a zygote, or other cell or tissue sample therefrom, to determine whether said bovine possesses one of the haplotypes of the present invention, some of which are indicative of improved milk production traits.

The method preferably is for haplotyping the bovine PI gene, which comprises identifying the sequence of nucleotides at positions 164, 269, 284, 407, and 989, for at least one copy of the PI gene and assigning to the individual a bovine PI haplotype, wherein the bovine PI haplotype is selected from the group consisting of the haplotypes shown in Table 1. The method may be used to identify the haplotype of both copies the PI gene in the animal, and assigning a haplotype pair to the animal.

One embodiment of a haplotyping method of the invention comprises examining one copy of the PI gene, or a fragment thereof, to identify the nucleotide at two or more polymorphic sites in that copy to assign a haplotype to the individual.

As will be readily appreciated by those skilled in the art, if a PI gene is cloned and sequenced any individual clone will typically only provide haplotype information on one of the two PI gene copies present in an individual. If haplotype information is desired for the individual's other copy, additional PI clones will usually need to be examined. Typically, at least five clones should be examined to have more than a 90% probability of haplotyping both copies of the PI gene in an individual.

Further provided is a method for genotyping the bovine PI gene, comprising determining for the two copies of the PI gene present the identity of the nucleotide pair at one or more polymorphic sites at positions 164, 269, 284, 407, and 989, wherein the one or more polymorphic sites (PS) have the position and alternative alleles shown in Table 1.

One embodiment of a genotyping method of the invention involves examining both copies of the PI gene, or a fragment thereof, to identify the nucleotide pair at one or more polymorphic sites listed in Table 1 in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at each of the polymorphic site listed in Table 1.

The present invention further provides a kit for haplotyping a bovine sample, the kit comprising in a container a nucleic acid molecule, as described above, designed for detecting the one or more of the polymorphisms listed in Table 1, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby haplotyping as described above is conducted on bovine embryos, and based on the results, certain cattle are either selected or dropped out of the breeding program. Most preferably, individuals carrying haplotype 1 is selected. The unexpected results of the present invention show that animals carrying haplotype 1 has improved milk production traits, including low SCS, high DPR and high productivity, as shown in Table 3. Haplotype 3 is positively correlated with fat yield. Haplotype 4 is positively correlated with milk yield and SCS and negatively correlated with DPR, and haplotype 5 is positively correlated with milk yield and SCS, and negatively correlated with fat percentage and protein percentage (tables 4, 5).

Through use of the linked marker loci, the different haplotypes can be manipulated in genetic improvement programs by procedures termed "marker assisted selection" (MAS), for genetic improvement within a breeding nucleus; or "marker assisted introgression" for transferring useful alleles from a resource population to a breeding nucleus (Soller 1990; Soller 1994).

The following examples are intended to illustrate preferred embodiments of the invention and should not be interpreted to limit the scope of the invention as defined in the claims.

EXAMPLES

Example 1: Identification of Haplotypes and Determination of their Association with Milk Production Traits Resource Population and Phenotypic Data The Cooperative Dairy DNA Repository (CDDR) is an extension of the Dairy Bull DNA Repository (DBDR) started at the University of Illinois in 1993. The DBDR was established to identify QTL in large Holstein families using the granddaughter design (Weller et al. 1990). In the granddaughter design, QTL are mapped using genotypes from grandsires and their sons and the granddaughters' phenotypic values as the trait endpoints. QTL can be mapped and markers flanking the QTL can be identified. Once flanking markers have been identified, marker-assisted selection can be utilized to shorten the generation interval and reduce time and cost of progeny testing.

Thirty seven (37) half-sib families comprised of 2,363 sons were selected from the CDDR collection for quantitative trait gene (QTG) detection using the granddaughter design. Data for Predicted Transmitting Abilities (PTA) of the traits of interest (protein yield, protein percentage, fat yield, fat percentage, milk yield, somatic cell score, daughter pregnancy rate, productive life) were obtained from the Animal Improvement Programs Laboratory (AIPL-USDA). The PTA includes the deviation of the daughter performance from the population mean adjusted for the genetic merit of mate and the genetic merit of the grandsire and grand dam (Van-Raden and Wiggans, 1991).

Previous efforts of QTL mapping on cattle chromosome 21 have revealed different QTL affecting production and health traits. Hayen et al. (1999) reported a putative QTL affecting milk yield and protein yield in linkage with the macrosatellite marker D21S27 at position 56 of chromosome 21. Rodriguez-Zas et al. (2002) reported that a QTL located at position 56 was associated with variations on somatic cell score (SCS) and protein yield. Mosig et al. (2001) reported a QTL that affected protein percentage at position 67.3. Accordingly, candidate genes in the chromosomal region of 10 cM, from position 57-67 were chosen for further investigation.

This region contains four characterized genes: CHGA, PI, AACT, and SERPINA3. The PI gene is further specifically chosen for investigation of its effect on milk production traits, because it has been reported that the PI protein is present in human milk and it might increase the survival of milk proteins by various mechanisms (Chowanadisai and Lonnerdal, 2002).

Polymorphism in PI Gene

It is necessary to determine whether polymorphism exists in this gene. Toward that goal, we amplified the total cDNA sequence of the gene from a wide range of cattle tissues. The complete cDNA sequence of bovine alpha 1-antitrypsin, or the proteinase inhibitor (PI) gene is known, and is available in the gene bank (Accession #X63129, Sinha et al., 1992, Biochim. Biophys. Acta 1130 (2), 209-212). The sequence (SEQ ID NO: 5) is shown in FIG. 1. Four primers based on the known PI sequence were designed. These primers are:

```
PI7
                                             (SEQ ID NO: 2)
5'-ATGGCACTCTCCATCACGCG 3'

PI11
                                             (SEQ ID NO: 3)
5'-CCACTAGCTTTGCACTCTCA 3'

PI9
                                             (SEQ ID NO: 4)
5'-TTGGACACCTTCAGAGGCTG 3'

PI0
                                             (SEQ ID NO: 5)
5'-AGTGTGAGAGCACGGGGAGA 3'
```

We amplified the total cDNA sequence of the gene from a wide range of cattle tissues. RT-PCR products from a wide range of tissues from five fetuses and five cows were analyzed by direct sequencing. The tissues were: heart, brain, lung, muscle, liver, kidney, pancreas, bone, cartilage, spleen, adrenal, mammary gland and ovary. Five polymorphic SNPs at positions 164, 269, 284, 407, and 989 were identified. Six different haplotypes could be determined from the five SNPs (See FIG. 1 and Table 1).

Selective Genotyping

Semen samples of 37 half-sib families comprised of 2,363 sons were selected from the CDDR collection for quantitative trait gene (QTG) detection using the granddaughter design.

For protein percentage trait, we used the selective DNA genotyping approach in order to reduce the costs of screening the population for polymorphic markers. In this approach, determination of association between a genetic marker and QTG is based on the distribution of the marker alleles among the samples of the extreme high and low phenotypic groups. Within each sire family, we choose 10% of the sons with highest PTAs for protein percentage and 10% of the sons with the lowest PTAs. A total of 423 individuals were chosen for selective genotyping analysis for protein percentage trait.

To search for associations with other traits of interest (see Table 3), we genotyped 1,258 individuals.

Single Nucleotide Polymorphism (SNP) Detection

Genomic DNA was extracted from semen samples with phenol/chloroform and proteinase k procedures (Kappes et al. 2000). The DNA concentration was measured using spectrophotometer Pro 2.1 (Pharmacia).

Primers were designed in the PI gene to amplify the total cDNA sequence of the gene. In order to detect polymorphisms in the PI gene exons, we extracted total RNA from a wide range of tissues by using RT-PCR.

RNA Extraction.

Cattle tissues were obtained from a local slaughterhouse. After dissection, tissues were immediately chilled on ice and submerged in an appropriate volume of RNALater RNA stabilization reagent (QIAGEN). Total RNA was extracted using the RNeasy kit (QIAGEN). The protocol for total RNA isolation from heart and muscle tissues was modified from the standard protocol for other tissues, due to the abundance of contractile proteins and collagen.

Sequencing of PCR and RT-PCR Products.

The sizes of PCR and RT-PCR products were estimated on a 1% agarose gel. The products were purified from the PCR solution, using GFX PCR DNA Purification Kit (Amersham Biosciences). Sequencing reactions consisted of 2 ul of BigDye Terminator mix (Applied Biosystems), 6 ul of dilution buffer (200 mM Tris HCl pH 9.0, 5 mM MgCl2), 5 pmol of primer, and 0.1 ug of template DNA in a final reaction volume of 20 ul. Cycle conditions were an initial denaturation at 96° for 3', then 50 cycles of 96° for 10", 58° for 4', followed by 7' at 72°. Excess dye terminators were removed using CleanSeq magnetic bead sequencing reaction clean up kit from Agencourt Biosciences. The samples were resuspended off of the beads in 50 ul of ddH2O. 10 ul of each sample was loaded into a 96 well PCR plate and loaded onto the sequencers according to the manufacturer's instructions. Samples were electrophoresed on an Applied Biosystems 3730XL automated DNA sequencing instrument, using 50 cm capillary arrays and POP-6 polymer. Data were analyzed using Applied Biosystems version 5.0 of Sequencing Analysis. SNPs were identified by visually inspecting each base in sequencing traces.

Inferring Haplotypes

Haplotypes were inferred as follows (Lagziel et al. 1996):
1. From homozygous individuals. For example, from an individual showing genotypes G/G, T/T, T/T, G/G, C/C, the haplotype GTTGC (HAPLOTYPE 4) was inferred;
2. From heterozygous individuals showing only a single heterozygous site. For example, from an individual having the genotype A/A, C/C, G/G, G/G, C/T, haplotypes ACGGC and ACGGT were inferred;
3. From direct sequencing of 30 sires. As shown in Table 2, five sires were homozygous for the five SNPs and 25 sires were heterozygous for at least one SNP. Six different haplotypes could be determined from the five SNPs; and
4. From direct sequencing of heterozygote and homozygote sons within each family. A total of 100 sons were sequenced.

Statistical Analysis

Analysis of variance (ANOVA) for each haplotype and trait combination was performed using the PROC GLM function of SAS (SAS Institute, Cary, N.C.).

TABLE 2

Genotypes and Haplotypes of 30 Sires as Determined by Direct Sequencing

| SIRE | 164 | 269 | 284 | 407 | 989 | HAPLOTYPE I | HAPLOTYPE II |
|------|-----|-----|-----|-----|-----|-------------|--------------|
| 1 | A/G | C | G | G/C | C/T | ACGCT (HAPLOTYPE 1) | GCGGC (HAPLOTYPE 5) |
| 2 | G | T | T | G | C/T | GTTGT (HAPLOTYPE 2) | GTTGC (HAPLOTYPE 4) |

TABLE 2-continued

Genotypes and Haplotypes of 30 Sires as Determined by Direct Sequencing

| SIRE | 164 | 269 | 284 | 407 | 989 | HAPLOTYPE I | HAPLOTYPE II |
|------|-----|-----|-----|-----|-----|-------------|--------------|
| 3 | G | T | T | G | C/T | GTTGT (HAPLOTYPE 2) | GTTGC (HAPLOTYPE 4) |
| 4 | A/G | C | G | G/C | C/T | ACGCT (HAPLOTYPE 1) | GCGGC (HAPLOTYPE 5) |
| 5 | A/G | C | G | G/C | C/T | ACGCT (HAPLOTYPE 1) | GCGGC (HAPLOTYPE 5) |
| 6 | A/G | C/T | G/T | G/C | C/T | ACGCT (HAPLOTYPE 1) | GTTGC (HAPLOTYPE 4) |
| 7 | A/G | C/T | G/T | G/C | C/T | ACGCT (HAPLOTYPE 1) | GTTGC (HAPLOTYPE 4) |
| 8 | A/G | C | G | G/C | C/T | ACGCT (HAPLOTYPE 1) | GCGGC (HAPLOTYPE 5) |
| 9 | A | C | G | C | C/T | ACGCT (HAPLOTYPE 1) | ACGCC (HAPLOTYPE 6) |
| 10 | G | C/T | G/T | G | C/T | GCGGT (HAPLOTYPE 3) | GTTGC (HAPLOTYPE 4) |
| 11 | A | C | G | C | C/T | ACGCT (HAPLOTYPE 1) | ACGCC (HAPLOTYPE 6) |
| 12 | G | C/T | G/T | G | C/T | GTTGT (HAPLOTYPE 2) | GCGGC (HAPLOTYPE 5) |
| 13 | G | C | G | G | C/T | GCGGT (HAPLOTYPE 3) | GCGGC (HAPLOTYPE 5) |
| 14 | A/G | C/T | G/T | G/C | C/T | ACGCT (HAPLOTYPE 1) | GTTGC (HAPLOTYPE 4) |
| 15 | A/G | C/T | G/T | G/C | C/T | ACGCT (HAPLOTYPE 1) | GTTGC (HAPLOTYPE 4) |
| 16 | A | C | G | C | C/T | ACGCT (HAPLOTYPE 1) | ACGCC (HAPLOTYPE 6) |
| 17 | A/G | C/T | G/T | G/C | C/T | ACGCT (HAPLOTYPE 1) | GTTGC (HAPLOTYPE 4) |
| 18 | A/G | C | G | G/C | C/T | ACGCT (HAPLOTYPE 1) | GCGGC (HAPLOTYPE 5) |
| 19 | G | T | T | G | C/T | GTTGT (HAPLOTYPE 2) | GTTGC (HAPLOTYPE 4) |
| 20 | A/G | C | G | G/C | C/T | ACGCT (HAPLOTYPE 1) | GCGGC (HAPLOTYPE 5) |
| 21 | G | C | G | G | C/T | GCGGT (HAPLOTYPE 3) | GCGGC (HAPLOTYPE 5) |
| 22 | G/A | C/T | G/T | G/C | C/T | ACGCT (HAPLOTYPE 1) | GTTGC (HAPLOTYPE 4) |
| 23 | G | C | G | G | C | GCGGC (HAPLOTYPE 5) | GCGGC (HAPLOTYPE 5) |
| 24 | A | C | G | C | C/T | ACGCT (HAPLOTYPE 1) | ACGCC (HAPLOTYPE 6) |
| 25 | G | C/T | G/T | G | C | GTTGC (HAPLOTYPE 4) | GCGGC (HAPLOTYPE 5) |
| 26 | G | T | T | G | C | GTTGC (HAPLOTYPE 4) | GTTGC (HAPLOTYPE 4) |
| 27 | G | C/T | G/T | G | C | GTTGC (HAPLOTYPE 4) | GCGGC (HAPLOTYPE 5) |
| 28 | G | T | T | G | C | GTTGC (HAPLOTYPE 4) | GTTGC (HAPLOTYPE 4) |
| 29 | G | T | T | G | C | GTTGC (HAPLOTYPE 4) | GTTGC (HAPLOTYPE 4) |
| 30 | A | C | G | C | T | ACGCT (HAPLOTYPE 1) | ACGCT (HAPLOTYPE 1) |

Analysis was performed for the combined data from all families segregating with the same haplotype.

The average allele substitution effects (a) were calculated following the method of Falconer and MacKay (1996) using:

$$\alpha = a + d(q-p)$$

where a and d are the homozygous and heterozygous genotypic values, respectively, and q and p are the allele frequencies of either of the two alleles of a bi-allelic polymorphic site of the gene.

The various traits are defined and measured according to the USDA standards set by the Animal Improvement Programs Laboratory (AIPL) of the United States Department of Agriculture. The total milk yield is measured in pounds (lb). Milk fat and protein content are measured as percentages. Productive life (PL) means duration of a cow in the milking herd before removal by voluntary, involuntary culling, or death. PL=Total months in milk limited to 10 months per lactation and 84 months of age. Somatic Cell Score=$\log_2$ (SCC, 100,000)+3; where SCC is somatic cells per milliliter. SCS of 3 is equal to 100,000 cells/ml. Lowest SCS is associated with lowest rates of mastitis infection (Schutz, 1994). Daughter Pregnancy Rate (DPR)=the percentage of non-pregnant cows that become pregnant during each 21-day period. A DPR of 1.0 implies that daughters are 1% more likely to become pregnant during a given 21 day estrus cycle than daughters of a bull with an evaluation of zero. An increase of 1% in PTA DPR equals a decrease of 4 days in PTA days open.

Results are shown in Tables 3 and 4. In Table 2 we presented genotyping and haplotyping results of the 30 available sires. As shown in Table 2, sires 1, 4, 5, 6, 7, 8, 9, 11, 14, 15, 16, 17, 18, 20, 22, 24, and 30 share haplotype 1 (ACGCT). A total of 759 sons of those sires were included in the analysis of haplotype 1. Table 3 shows the ANOVA analysis of these 17 sire families. Since all sons share one common haplotype (ACGCT), we determined haplotypes in these sons according to a single genotype at position 989. Three possible genotypes were designated: TT for individuals homozygous at position 989 (and by inference are also homozygous for haplotype 1), CT for individuals heterozygous at position 989 (also heterozygous for haplotype 1), CC for individuals homozygous for other haplotypes. Table 3 also shows the mean genetic values of the different genotypes TT, CT, and CC. Table 4 shows the ANOVA analysis of all haplotypes with significant effects. Table 5 shows the allele substitution effects found associated with the different haplotypes (Falconer, 1996). The signs + and − indicate whether the effect of the haplotype is positive or negative. It is noteworthy that negative effects on SCS are desirable, since lowest SCS is associated with lowest rates of mastitis infection.

Example 2: Experimental Design for Identification of Haplotypes

The following is exemplifies experimental designs for determining haplotypes of a sample. Genomic DNA from the sample may be first amplified via PCR with primers PI9, PI10 followed with restriction enzyme RsaI. This enzyme digests C allele only at position 989, so that TT products would not be digested, while CT and CC products would be digested.

Haplotype 1 can then be differentiated from 2 and 3 by specific primer amplification at position 164, by designing a primer that ends with A or G.

Haplotype 2 can be differentiated from 3 by specific primer amplification at position 269 or 285.

Haplotype 6 can be differentiated from 4 and 5 by position 164.

Haplotype 4 can be differentiated from 5 by positions 269 and 285.

TABLE 3

Comparison of Various Traits Between Haplotype 1 (TT) and Other Haplotypes

| Trait | ANOVA analysis P | Mean/ genotype TT | CT | CC | Contrast analysis TT vs. others | CC vs. others | Regression analysis p |
|---|---|---|---|---|---|---|---|
| PTA milk | 0.8119 | 443.18 | 480.15 | 450.89 | 0.73 | 0.87 | 0.8914 |
| PTA fat | 0.6194 | 19.084 | 17.135 | 17.929 | 0.44 | 0.93 | 0.6094 |
| PTA fat % | 0.2494 | 0.01455 | 0.0005 | 0.008 | 0.24 | 0.95 | 0.4882 |
| PTA prot. | 0.21818 | 21.689 | 19.492 | 18.255 | 0.1153 | 0.2110 | 0.1194 |
| PTA prot. % | 0.0013 | 0.036 | 0.023 | 0.020 | 0.0003 | 0.042 | 0.0015 |
| PTA PL[1] | <0.0001 | 0.4078 | 0.2160 | −0.2248 | <0.0001 | <0.0001 | <0.0001 |
| PTA SCS[2] | <0.0001 | 3.0923 | 3.1073 | 3.1836 | 0.0003 | <0.0001 | <0.0001 |
| PTA DPR[3] | 0.0103 | 0.315 | 0.176 | −0.009 | 0.0069 | 0.0045 | 0.0027 |
| DYD milk | 0.5423 | 397.23 | 461.01 | 397.9 | 0.65 | 0.67 | 0.9274 |
| DYD fat | 0.747 | 18.294 | 16.579 | 16.731 | 0.476 | 0.772 | 0.5625 |
| DYD fat % | 0.181 | 0.0185 | 0.0015 | 0.0117 | 0.222 | 0.866 | 0.4948 |
| DYD milk prot. | 0.478 | 388.69 | 451.85 | 375.53 | 0.723 | 0.549 | 0.9580 |
| DYD prot. | 0.2174 | 20.27 | 18.44 | 16.05 | 0.11 | 0.10 | 0.0822 |
| DYD prot. % | 0.0014 | 0.0371 | 0.0215 | 0.0215 | 0.0005 | 0.101 | 0.0035 |
| DD[5] SCS | <0.0001 | −0.0066 | 0.0127 | 0.107 | 0.0016 | <0.0001 | <0.0001 |
| DD DPR | 0.1961 | 0.0396 | 0.0169 | 0.0076 | 0.071 | 0.210 | 0.0847 |

[1] Productive life;
[2] somatic cell score;
[3] daughter pregnancy rate;
4- daughter yield deviation;
[5] daughter deviation

TABLE 4

ANOVA Analysis (p Values) of All haplotypes Affecting Different Traits

| Trait (PTA) | Haplotype 1 (ACGCT) N = 759 | Haplotype 2 (GTTGT) N = 184 | Haplotype 3 (GCGGT) N = 130 | Haplotype 4 (GTTGC) N = 455 | Haplotype 5 (GCGGC) N = 447 | Haplotype 6 (ACGCC) N = 123 |
|---|---|---|---|---|---|---|
| Milk Yield | | 0.0232 | | 0.081 | 0.0035 | |
| Fat Yield | | | 0.0182 | | | |
| Milk Fat % | | | | | 0.0095 | |
| Protein Yield | | 0.0234 | | | 0.0920 | |
| Milk Protein % | 0.0013 | | | | 0.0069 | |
| Productive Life | <0.0001 | | | | | 0.0240 |
| SCS | <0.0001 | | | 0.0323 | 0.0241 | 0.0303 |
| DPR | 0.0103 | | | 0.0051 | | |
| DYD milk | | 0.0116 | | 0.0291 | 0.0030 | |
| DYD fat | | | | | | |
| DYD fat % | | | | | 0.0296 | |
| DYD milk prot. | | 0.0106 | | 0.0290 | 0.0054 | |
| DYD protein | | 0.0199 | | | | |
| DYD protein % | 0.0014 | | | | 0.0198 | |
| DD productive life | <0.0001 | | | | 0.0478 | 0.0387 |
| DD SCS | <0.0001 | | | 0.0764 | | 0.0335 |
| DD DPR | | | | | 0.0276 | |

TABLE 5

Allele Substitution Effects of All Haplotypes And Selected Milk Production Traits

| Trait | Haplotype 1 (ACGCT) N = 759 | Haplotype 2 (GTTGT) N = 184* | Haplotype 3 (GCGGT) N = 130* | Haplotype 4 (GTTGC) N = 455 | Haplotype 5 (GCGGC) N = 447 | Haplotype 6 (ACGCC) N = 123* |
|---|---|---|---|---|---|---|
| Milk Yield | | (−) | | 199.00(+) | 380(+) | |
| Fat Yield | | | (+) | | | |
| Milk Fat % | | | | 0.044(+) | −0.0294(−) | |
| Protein Yield | | (−) | | | | |
| Milk Protein % | 0.012(+) | | | 0.013(−) | −0.019(−) | |
| Productive Life | 0.6974(+) | | | 0.318(−) | | (−) |

TABLE 5-continued

Allele Substitution Effects of All Haplotypes And Selected Milk Production Traits

| Trait | Haplotype 1 (ACGCT) N = 759 | Haplotype 2 (GTTGT) N = 184* | Haplotype 3 (GCGGT) N = 130* | Haplotype 4 (GTTGC) N = 455 | Haplotype 5 (GCGGC) N = 447 | Haplotype 6 (ACGCC) N = 123* |
|---|---|---|---|---|---|---|
| SCS | 0.1074(−) | | | 0.0492(+) | | (+) |
| DPR | 0.3366(+) | | | −0.460(−) | | (−) |
| DD productive life | | | | | −0.360(−) | |

*Due to small number of individuals, allele substitution effects values were not included.
(+), positive effect; (−), negative effect.

REFERENCES

1. Weller, J., Kashi, Y. and Soller, M. (1990). Daughter and granddaughter design for mapping of quantitative trait loci in dairy cattle. J. Dairy Sci. 73:2525-2537.
2. VanRaden, P. M., and Wiggans, G. R. (1991). Derivation, calculation, and the use of National Model Information. J. Dairy Sc. 74:2737-2746
3. Kappes, S. M., Bennett, G. L., Keele, J. W., Echternkamp, S. E., Gregory, K. E. and Thallman. R. M. (2000). Initial results of genomic scans for ovulation rate in a cattle population selected for increased twinning rate. J Anim Sci. 78:3053-3059.
4. Lagziel, A., Lipkin, E. and Soller, M. (1996). Association between SCCP haplotypes at the bovine growth hormone gene and milk protein percentage. Genetics 142:945-951.
5. Falconer, D. S. and Mackay F. C. (1996). Introduction to Quantitative Genetics. 4th ed. Longman Scientific and Technical, New York.
6. Heyen, D. W., Weller, J. I., Ron, M., Band, M. and Beever J. E. et al. (1999). A genome scan for QTL influencing milk production and health traits in dairy cattle. Physiol. Genomics 1:165-175.
7. Rodriguez-Zas, S. L., Southey, B. R., Heyen, D. W. and Lewin H A (2002). Interval and composite interval mapping of somatic cell score, yield, and components of milk in dairy cattle. J Dairy Sci. 85:3081-3091.
8. Mosig, M. O., Lipkin, E., Khutoreskaya, G., Tchourzyna, E., Soller, M. and Friedmann A. (2001). A whole genome scan for quantitative trait loci affecting milk protein percentage in Israeli-Holstein cattle, by means of selective milk DNA pooling in a daughter design, using an adjusted false discovery rate criterion. Genetics. 157: 1683-98.
9. Chowanadisai, W. and Lonnerdal, B. (2002). Alpha(1)-antitrypsin and antichymotrypsin in human milk: origin, concentrations, and stability. Am J Clin Nutr. 76:828-833.
10. Soller, M. (1990) Genetic mapping of the bovine genome using DNA-level markers with particular attention to loci affecting quantitative traits of economic importance. J. Dairy Sci. 73:2628-2646.
11. Soller, M. (1994) Marker-assisted selection, an overview. Anim. Biotech. 5:193-208.
12. Schutz, M. (1994) Genetic evaluation of somatic cell scores for United States dairy cattle. J. D. Sci. 77:2113-2129

What is claimed is:

1. A method for selectively breeding cattle using a multiple ovulation and embryo transfer (MOET) procedure, the method comprising:
   superovulating a female bovine animal;
   collecting eggs from said superovulated female bovine animal;
   in vitro fertilizing said eggs;
   implanting the fertilized eggs into another female bovine animal and allowing for an embryo to develop;
   detecting the presence of a proteinase inhibitor (PI) gene haplotype in the developing embryo comprising:
   (i) detecting the presence of a wildtype haplotype, wherein a wildtype haplotype comprises the nucleotides G, C, G, G and C at the positions corresponding to positions 164, 269, 284, 407 and 989, respectively, of SEQ ID NO: 1;
   (ii) detecting the presence of haplotype 1, wherein haplotype 1 comprises the nucleotides A, C, G, C and T at the positions corresponding to positions 164, 269, 284, 407 and 989, respectively, of SEQ ID NO: 1;
   (iii) detecting the presence of haplotype 2, wherein haplotype 2 comprises the nucleotides G, T, T, G and T at the positions corresponding to positions 164, 269, 284, 407 and 989, respectively, of SEQ ID NO: 1;
   (iv) detecting the presence of haplotype 3, wherein haplotype 3 comprises the nucleotides G, C, G, G and T at the positions corresponding to positions 164, 269, 284, 407 and 989, respectively, of SEQ ID NO: 1;
   (v) detecting the presence of haplotype 4, wherein haplotype 4 comprises the nucleotides G, T, T, G and C at the positions corresponding to positions 164, 269, 284, 407 and 989, respectively, of SEQ ID NO: 1;
   (vi) detecting the presence of haplotype 5, wherein haplotype 5 comprises the nucleotides G, C, G, G and C at the positions corresponding to positions 164, 269, 284, 407 and 989, respectively, of SEQ ID NO: 1; or
   (vii) detecting the presence of haplotype 6, wherein haplotype 6 comprises the nucleotides A, C, G, C and C at the positions corresponding to positions 164, 269, 284, 407 and 989, respectively, of SEQ ID NO: 1;
   and terminating the developing embryo if the developing embryo is not haplotype 1, haplotype 3, haplotype 4 or haplotype 5.

2. The method of claim 1, further comprising terminating the developing embryo if the developing embryo is not haplotype 1.

3. A method for selectively breeding dairy cattle, the method comprising:
   obtaining a genomic DNA sample from a bull;
   detecting in said genomic DNA the presence of homozygous haplotype 1 in the PI gene, wherein haplotype 1 comprises the nucleotides A, C, G, C and T at the positions corresponding to positions 164, 269, 284, 407 and 989, respectively, of SEQ ID NO: 1; and
   using semen from said bull for fertilizing a female animal.

4. The method according to claim 3, wherein the female animal is in vitro fertilized with semen from said bull.

5. The method according to claim 3, wherein a MOET procedure is used to fertilize said female animal.

6. The method according to claim 3, where said female animal is also homozygous for haplotype 1 in the PI gene.

* * * * *

```
                        SEQUENCE LISTING

<160> NUMBER OF SEQ ID NOS: 6

<210> SEQ ID NO 1
<211> LENGTH: 1380
<212> TYPE: DNA
<213> ORGANISM: Bos taurus

<400> SEQUENCE: 1
gaccagccct gacctaggac agtgaatcga taatggcact ctccatcacg cggggccttc      60
tgctgctggc agccctgtgc tgcctggccc ccatctccct ggctggagtt ctccaaggac     120
acgctgtcca agagacagat gatacatccc accaggaagc agcgtgccac aagattgccc     180
ccaacctggc caactttgcc ttcagcatat accaccattt ggctcatcag tccaacacca     240
gcaacatctt cttctccccc gtgagcatcg cttcagcctt tgcgatgctc tccctgggag     300
ccaagggcaa cactcacact gagatcctga agggcctggg tttcaacctc actgagctcg     360
cagaggctga gatccacaaa ggctttcagc atcttctcca caccctgaac cagccaaacc     420
accagctgca actgaccact ggcaatggtc tgttcatcaa tgagagtgca aagctagtgg     480
atacgttttt ggaggatgtc aagaacctgt atcactccga agccttctcc atcaacttca     540
gggatgctga ggaggccaag aagaagatca acgattatgt agagaaggga agccatggaa     600
aaattgtgga gttggtaaag gttcttgacc caaacacagt ttttgctctg gtgaattaca     660
tttcctttaa aggaaaatgg gagaagccct tcgagatgaa gcacaccaca gagagggact     720
```

```
tccatgtgga cgagcaaacc actgtgaagg tgcccatgat gaaccgcctg ggcatgtttg    780
acctccacta ctgcgacaag ctcgccagct gggtgctgct gttggactac gtgggcaacg    840
tcaccgcctg cttcatcctg cccgacctgg ggaaactgca gcagctggag gacaagctca    900
acaacgaact cctcgccaag ttcctggaaa agaaatatgc aagttctgcc aatttacatt    960
tgcccaaact gtccatttct gaaacgtacg atctaaaaag tgtcctgggc gatgtgggca   1020
tcaccgaggt cttcagcgat agggctgacc tctcagggat caccaaggaa cagcctctga   1080
aggtgtccaa ggctctccac aaggctgcac tgaccatcga tgagaaaggg acagaagctg   1140
tcgggtccac gtttctggaa gccatcccca tgtcccttcc cccagacgtc gagttcaaca   1200 gaccttcct ctgcatcctc tacgacagaa acaccaaatc tcccctcttc gtgggaaagg   1260
tggtgaatcc cacccaagcc taactgcctc tcggagttca gccttcccct cccaggccag   1320 gtcccccac tccctccatg gcattaaagg atgactgacc tagccccgaa aaaaaaaaaa   1380
```

<210> SEQ ID NO 2  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 2
atggcactct ccatcacgcg                                                  20

<210> SEQ ID NO 3  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 3
ccactagctt tgcactctca                                                  20

<210> SEQ ID NO 4  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 4
ttggacacct tcagaggctg                                                  20

<210> SEQ ID NO 5  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 5
agtgtgagag cacggggaga                                                  20

<210> SEQ ID NO 6  
<211> LENGTH: 977  
<212> TYPE: DNA  
<213> ORGANISM: Bos taurus

<400> SEQUENCE: 6

-continued

```
cagaccgacc cgggagctgc cacatctggt tcagtcagag ggtgggggga tagacccacc        60
gaccacggcc atgaccgctg tgtgtctgct tccaacagag gccagaatgc atgcacgtgg       120
taccaggcag actccatggg agggctggtg cccaggggtr aggagtgaaa gtcctgtcct       180
tgaggacgtc ctccccagcc tggaaactgc ccgttcctgg tgcacaggga aagcaatgtc       240
aaattcatgt tgttggcaaa cccagaaaga agaggatgga cttttggca aaggtggcag        300 ttgaatgtag attacaggat agagtgtgga ttacaggcta aaaagtccac ggcaggatgg       360
gggcggggga ggggaggata atgcttggag cattatccaa gataatgctg aaaaagccaa      420
cgcccagagc aggaaactcc agcacctgtt tgaggctggt tctgattcct ctgtcattag       480
atgagtgtgg ttcgaccagg tccccatcat gcactccata tcagtacctg tctctgtgtt      540
tgtagatatg cccaggcccg gatgagcaat tttatcatgt ataacataaa acaaagatga      600
aaatacagaa aagtactcct cacgccctct acagacgtca ctcaggacct accaccacac      660
cccacagtcc cctgggatcc tggccctggg ggagtcccag tctagcgggt gtgatgaaac      720
cctacaggga agtagtgagt acagtccttc cagaagacac cccagatctc caggaggcct      780
tctcagagga ggtggccctt gagaggctct gcaggacaag aggatggccc tgattctaat      840
atcctctgac cctgggcata gaggaactaa aagtggaata aaccaaagtg tgagagcacg      900
gggagagggc accaactgga aagaacaacc ggaaaaggaa gctctttcac tctgtgactt      960 tttttttcc actacag                                                     977
```